US007341592B1

(12) United States Patent
Walters et al.

(10) Patent No.: US 7,341,592 B1
(45) Date of Patent: Mar. 11, 2008

(54) METHOD AND APPARATUS FOR GRAFT FIXATION

(75) Inventors: Troy M Walters, Plymouth, IN (US); Kevin T Stone, Winona Lake, IN (US); Jason D Meridew, Syracuse, IN (US)

(73) Assignee: Biomet Sports Medicine, Inc., Warsaw, IN (US)

( * ) Notice: Subject to any disclaimer, the term of this patent is extended or adjusted under 35 U.S.C. 154(b) by 510 days.

(21) Appl. No.: 10/686,236

(22) Filed: Oct. 15, 2003

(51) Int. Cl.
*A61B 17/00* (2006.01)

(52) U.S. Cl. ........................................ 606/79
(58) Field of Classification Search ................. 606/53, 606/79, 86, 87, 96, 99; 623/13.11, 13.12, 623/13.13, 13.14, 13.17
See application file for complete search history.

(56) References Cited

U.S. PATENT DOCUMENTS

| | | | |
|---|---|---|---|
| 2,695,607 A | 11/1954 | Hipps et al. | |
| 3,871,379 A | 3/1975 | Clarke | |
| D249,705 S | 9/1978 | London | |
| 4,257,411 A | 3/1981 | Cho | |
| 4,535,768 A | 8/1985 | Hourahane et al. | |
| 4,922,897 A | 5/1990 | Sapega et al. | |
| 4,985,032 A | 1/1991 | Goble | |
| 4,998,937 A | 3/1991 | Grimes | |
| 5,004,474 A | 4/1991 | Fronk et al. | |
| 5,030,219 A | 7/1991 | Matsen, III et al. | |
| 5,098,435 A | 3/1992 | Stednitz et al. | |
| 5,108,396 A | 4/1992 | Lackey et al. | |
| 5,112,336 A | 5/1992 | Krevolin et al. | |
| 5,129,902 A | 7/1992 | Goble et al. | |
| 5,201,744 A | 4/1993 | Jones | |
| 5,234,434 A | 8/1993 | Goble et al. | |
| 5,234,444 A | 8/1993 | Christoudias | |
| 5,257,996 A | 11/1993 | McGuire | |
| 5,266,075 A | 11/1993 | Clark et al. | |
| 5,300,077 A | 4/1994 | Howell | |

(Continued)

FOREIGN PATENT DOCUMENTS

EP    1 360 949    11/2003

(Continued)

*Primary Examiner*—Anuradha Ramana
(74) *Attorney, Agent, or Firm*—Harness, Dickey & Pierce, P.L.C.

(57) ABSTRACT

An apparatus and method for performing a surgery, especially an ACL replacement surgery, where a flexible strand insertion rod co-operates with a U-Guide apparatus to insert a flexible strand into a tunnel formed in a bone portion and to guide a pair of drill points to form a pair of tunnels transversely to the tunnel of the insertion rod. The drill points are guided through the insertion rod and the flexible strand is held over the drill points as the transverse tunnels are formed. The insertion rod is then removed from the tunnels formed in the bone and the flexible strand is held looped over the second drill point. Subsequently, a soft tissue replacement is affixed to one end of the flexible strand and pulled over up to the first drill point with the other end of the flexible strand. The first drill point is then used to pull a cross pin through the transverse tunnel to hold the looped end of the soft tissue replacement in place. Finally, the two free ends of the soft tissue replacement are affixed to the bone completing the implantation of a soft tissue replacement.

20 Claims, 6 Drawing Sheets

U.S. PATENT DOCUMENTS

| | | |
|---|---|---|
| 5,350,380 A | 9/1994 | Goble et al. |
| 5,354,300 A | 10/1994 | Goble et al. |
| 5,356,413 A | 10/1994 | Martins et al. |
| 5,393,302 A | 2/1995 | Clark et al. |
| 5,397,356 A | 3/1995 | Goble et al. |
| D357,534 S | 4/1995 | Hayes |
| 5,423,823 A | 6/1995 | Schmieding |
| 5,431,651 A | 7/1995 | Goble |
| 5,437,677 A | 8/1995 | Shearer et al. |
| 5,454,365 A | 10/1995 | Bonutti |
| 5,562,671 A | 10/1996 | Goble et al. |
| 5,601,562 A | 2/1997 | Wolf et al. |
| 5,643,273 A | 7/1997 | Clark |
| 5,674,224 A | 10/1997 | Howell et al. |
| 5,849,013 A | 12/1998 | Whittaker et al. |
| 5,891,150 A * | 4/1999 | Chan ............ 606/96 |
| 5,895,425 A | 4/1999 | Grafton et al. |
| 5,918,604 A | 7/1999 | Whelan |
| 5,931,839 A | 8/1999 | Medoff |
| 6,039,739 A | 3/2000 | Simon |
| 6,066,173 A | 5/2000 | McKernan et al. |
| 6,110,211 A | 8/2000 | Weiss |
| 6,113,604 A | 9/2000 | Whittaker et al. |
| 6,132,433 A | 10/2000 | Whelan |
| 6,231,611 B1 | 5/2001 | Mosseri |
| 6,306,138 B1 | 10/2001 | Clark et al. |
| 6,325,804 B1 | 12/2001 | Wenstrom, Jr. et al. |
| 6,342,056 B1 | 1/2002 | Mac-Thiong et al. |
| 6,371,124 B1 | 4/2002 | Whelan |
| 6,375,684 B1 | 4/2002 | Kriek |
| 6,379,384 B1 | 4/2002 | McKernan et al. |
| 6,494,913 B1 | 12/2002 | Huebner |
| 6,497,726 B1 | 12/2002 | Carter et al. |
| 6,517,546 B2 * | 2/2003 | Whittaker et al. ............ 606/98 |
| 6,537,319 B2 | 3/2003 | Whelan |
| 6,562,071 B2 | 5/2003 | Jarvinen |
| 6,589,281 B2 | 7/2003 | Hyde, Jr. |
| 6,673,115 B2 | 1/2004 | Resch et al. |
| 6,712,823 B2 | 3/2004 | Grusin et al. |
| 6,733,529 B2 | 5/2004 | Whelan |
| 6,752,830 B1 | 6/2004 | Goble et al. |
| 7,033,364 B1 * | 4/2006 | Walters et al. ................ 606/99 |
| 2001/0047210 A1 | 11/2001 | Wolf |
| 2001/0053934 A1 | 12/2001 | Schmieding |
| 2002/0019635 A1 | 2/2002 | Wenstrom, Jr. et al. |
| 2002/0087160 A1 | 7/2002 | Clark et al. |
| 2002/0099381 A1 | 7/2002 | Maroney |
| 2002/0111689 A1 | 8/2002 | Hyde, Jr. |
| 2002/0111690 A1 | 8/2002 | Hyde |
| 2002/0133153 A1 | 9/2002 | Hyde, Jr. |
| 2002/0138148 A1 | 9/2002 | Hyde, Jr. |
| 2002/0138149 A1 | 9/2002 | Hyde, Jr. |
| 2003/0097179 A1 | 5/2003 | Carter et al. |
| 2003/0163202 A1 | 8/2003 | Lakin |
| 2004/0092936 A1 | 5/2004 | Miller et al. |

FOREIGN PATENT DOCUMENTS

| | | |
|---|---|---|
| FR | 2 684 543 | 6/1993 |

* cited by examiner

METHOD AND APPARATUS FOR GRAFT FIXATION

FIELD OF THE INVENTION

The present invention relates to endoscopic soft tissue replacement fixation. More particularly, the present invention relates to an apparatus and a method to reconstruct an anterior cruciate ligament with soft tissue replacements within a femoral tunnel.

BACKGROUND OF THE INVENTION

The knee joint is frequently the object of injury and is often repaired using arthroscopic surgical procedures. An example of such arthroscopic surgical procedure is the replacement of anterior cruciate ligaments of the knee. The tearing of these ligaments is common in sports activities such as football or skiing.

Currently, fascia lata soft tissue replacements are flexible strands which are affixed to a threaded stud and turned into the femoral tunnel. Unfortunately, this procedure may result in the soft tissue replacement being wrapped upon itself during insertion. Hamstring soft tissue replacements are also currently fixed over a screw in the tibial tunnel and fixed on the lateral femur. This technique requires the femoral tunnel to completely penetrate the femur. In addition, according to present procedures, fixation of the soft tissue replacement on the femoral side requires a large incision.

It has been difficult to insert and fasten a soft tissue replacement in a blind hole or tunnel. Attempts have been made to thread the soft tissue replacement through the tunnel and over an anchor, but with some difficulty. Thus far, the prior art has not developed a quick and efficient way to implant a soft tissue replacement over an implanted anchoring system.

While offering certain improvements in arthroscopic surgery to repair ligaments, the prior art may still be improved upon to overcome the limitations on the endoscopic hamstring soft tissue replacement fixation due, in many instances, to the weakness of the flexible strand used to span the gap between the tendon soft tissue replacement and the fixation post.

Other techniques attempt to use biological fixation to augment or replace mechanical fixation. While increasing fixation strength these techniques require time to fully realize their fixation potential. Additionally the techniques may take additional surgical time and resources that a purely mechanical fixation technique may not require.

SUMMARY OF THE INVENTION

An apparatus including a member that acts as a flexible strand insertion and guide rod is used to increase the simplicity and effectiveness of a soft tissue implant procedure. The member inserts a flexible strand, which has been preloaded onto the insertion rod, into a blind tunnel formed in a bone structure and provides a guide for first and second drill points or bits. Thus the member may be removed with the flexible strand already positioned in place to pull an implant into the blind tunnel over the first drill point and adjacent the second drill point. The second drill point is then removed, allowing the implant to be easily pulled over the first drill point. A cross or set pin is then pulled after the drill point into the drill hole to lock the implant in place.

A first embodiment includes an apparatus to position a flexible strand in a tunnel, having a diameter, formed in a bone while performing a surgery. The apparatus comprises a guide member extending along a first axis and having a first end and second end. The guide member includes a guide portion defining an area, extending from the first end and along the first axis. The guide portion includes a first leg and a second leg, the first leg and the second leg define a slot disposed therebetween, wherein the slot defines a first plane. The first leg further defines a first groove and the second leg defines a second groove; wherein the first groove extends along a distal end of the first leg and along a length of the first leg and the second groove extends along a distal end of the second leg and along a length of the second leg. The first groove and the second groove are adapted to receive the flexible strand. The apparatus further has a second guide member fixed parallel to the first member. The second member has a pair of guide holes configured to guide first and second adjacent drill points.

A second embodiment of the apparatus includes an apparatus to place a flexible strand in a tunnel, having a diameter, formed in bone while performing a surgery. The apparatus comprises a first member having a first end and a second end spaced apart. The first end defines a slot, adapted to guide an instrument, wherein the slot lies in a first plane. The first end further defines a groove, wherein the groove lies in a second plane. The first plane and the second plane intersect. A second member having a first end and a second end, the second member defines first and second passages positioned adjacent the first end. The first member extends adjacent to the second end of the second member; wherein the first end of the first member and the passage are generally aligned.

The apparatus allows a method of performing an implant procedure. A method of surgically implanting a soft tissue replacement for attaching two bone members comprises inserting an insertion rod having a flexible strand pre-loaded on the insertion rod into a first tunnel. Next, forming second and third tunnels transverse and through the first tunnel and the insertion rod with a tool bit. Next, retaining the flexible strand within the first tunnel. The method also includes removing the insertion rod from the second tunnel and retracting the flexible strand.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the embodiments is merely exemplary in nature and is in no way intended to limit the invention, its application, or uses. Moreover, while the present invention is discussed in detail below with regard to ACL reconstruction, those skilled in the art will recognize the other types of soft tissue fixation may employ the present invention.

Figure 1:
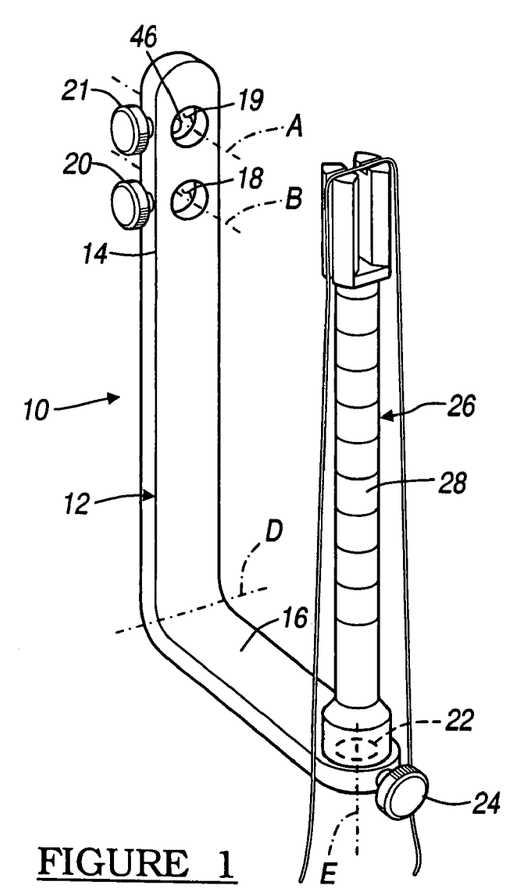
FIG. 1 is a perspective view of the bone insertion rod affixed to a U-Guide.

Referring to FIG. 1, a guide apparatus 10, which may be generally U-shaped, includes an L-shaped retaining bar or L-guide 12 that includes two portions or legs, a first portion 14 and a second portion 16, that is substantially perpendicular to the first portion 14. The first portion 14 defines a first guide section 18 and a second guide section 19, formed transversely through the first portion 14. The guide section may be passage through or transverse to the first portion 14 such as a bore wherein the guide section ledge would be a bore ledge. A pair of set screws 20 and 21 are provided to create a locking mechanism for the guide sections 18 and 19. The second portion 16 defines a bore 22 formed transversely through the second portion 16. A set screw 24 is also provided to create a locking mechanism for the bore 22. The L-guide 12 is shown in an L-shape, however, it will be understood the L-guide 12 may be any appropriate form. Generally, however, the axes defining the guide section 18 and the bore 22 are orthogonal. Therefore, the first and second axis A and B of the guide section 18 should intersect the second axis E of the bore 22 at a right angle.

An insertion or guide rod 26 is adjustably held in the bore 22 and locked in place with the set screw 24. With continuing reference to FIG. 1 and further reference to FIG. 2, the insertion rod 26 includes a body portion 28. The body portion 28 is substantially cylindrical and formed around a longitudinal axis C. The body portion 28, which is generally a solid, may also taper towards the guide portion 36 (described herein). Also, the body portion 28 may include depth indicia 29 to give a visual indication of the depth of the insertion rod 26 into a patient.

Figure 2:
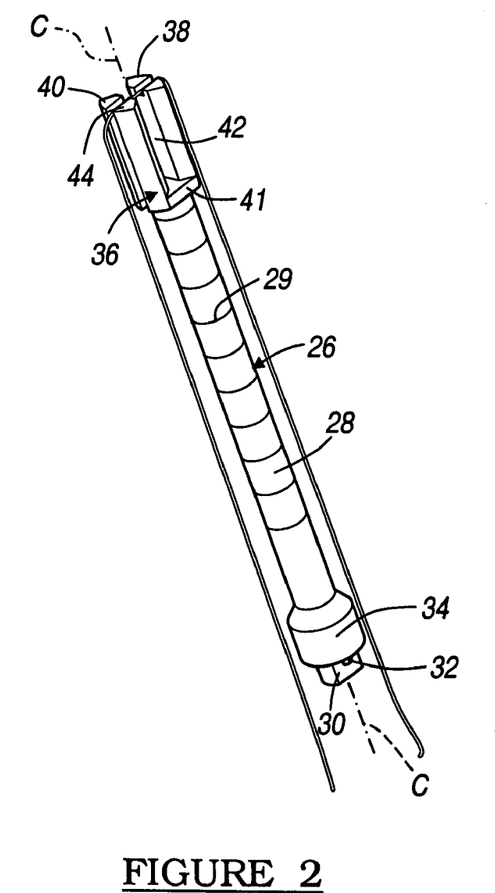
FIG. 2 is a perspective view of bone insertion rod not affixed to the U-Guide.

Extending from a first end of the body portion 28 is an L-Guide engaging portion 30 which includes a notch or projection 32 that is received in the second portion 16 of the L-Guide 12 to ensure proper orientation of the insertion rod 26 to the L-Guide 12. The notch 32 on the insertion rod 26 is keyed to be received on to a portion of the second portion 16. The insertion rod 26 further includes a collar 34, to ensure that the insertion rod 26 is held at a predetermined depth in the L-Guide 12 and to further ensure proper orientation of the insertion rod 26 relative to the L-Guide 12.

A guide portion 36 extends from a second end of the body portion 28. The guide portion 36 includes two generally parallel legs 38 and 40 and a shoulder 41. Each leg 38, 40 extends from the body portion 28 along axis C, though offset therefrom. The two legs 38, 40 define a slot 42, where the slot 42 extends substantially the distance of the two legs 38, 40 and meet at the shoulder 41. Also formed in each of the legs 38, 40 is a flexible strand groove 44. The flexible strand groove 44 may be any appropriate depth, but exemplary is substantially equal in depth to the diameter of a cord or flexible strand thread or suture to be used with the apparatus 10.

The insertion rod 26 may be any desired length. Preferably, however, the distance between the collar shoulder 34 and the shoulder 41 is equal to the distance between a first end of the first portion 14, generally represented by line D, and the guide section 19. In this way, the guide section ledge 19 and the slot 42 are generally equidistant from the second portion 16. Therefore, any instrument received through the guide section 19 would remain substantially parallel to the second portion 16 when it passed through the slot 42.

The flexible strand groove 44 is placed orthogonally to the slot 42 so that a cord, such as a flexible strand, may be placed in the flexible strand groove 44 to form an enclosed passage for any device that may be placed through the slot 42. In this way, a device such as a K-Wire (described herein), when inserted through the slot 42 has a flexible strand looped over the K-Wire. It will be understood, however, that the flexible strand groove 44 may be formed at any orientation relative to the slot 42 as long as a flexible strand placed in the flexible strand groove 44 will overlay the slot 42.

The notch 32 ensures that the insertion rod 26 is properly oriented with the L-Guide member 12 of the U-guide apparatus 10. In particular, the slot 42 is preferably aligned with the guide sections 18 and 19. The set screw 24 tightens against the L-Guide engaging portion 30 to ensure that the insertion rod 26 does not move during a surgical procedure. Also, this ensures the proper keyed fit of the notch 32 into the second portion 16 so that the guide section 18 and the slot 42 are properly aligned. This ensures that the instrument received through the apparatus 10 is aligned. It will be understood, however, that any appropriate means may be used to secure the insertion rod 26 to the L-Guide member 12 of the apparatus 10.

Referring to the remaining FIGS. 3-11, an exemplary method for using the apparatus 10, including the insertion rod 26 is described. It will be understood that although the apparatus 10 is described in the use of an Anterior Cruciate Ligament (ACL) replacement, any appropriate surgery may be performed with the apparatus 10 which would require its attributes.

Figure 3:
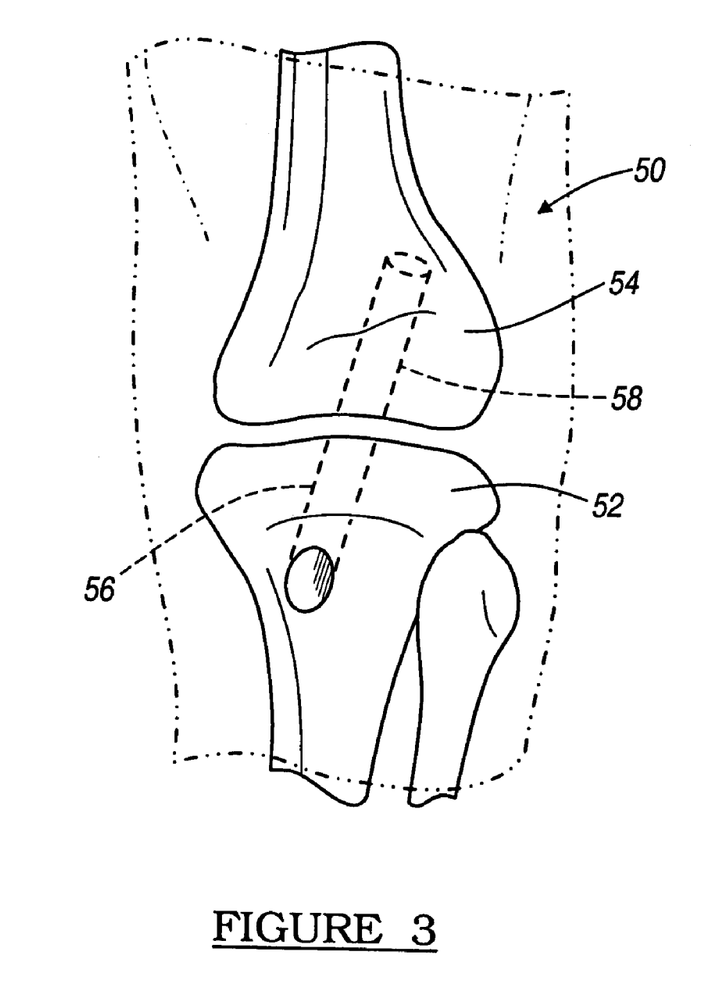
FIG. 3 is an exemplary view of a knee prepared for insertion of the insertion rod.

With particular reference to FIG. 3, a knee 50 generally includes at least a tibia 52 and a femur 54 surrounded by soft tissue 55. The knee 50 is initially prepared by forming a tibial tunnel 56 and a femoral tunnel 58 which are substantially in line with one another such that a straight and solid object could engage both the tibial tunnel 56 and the femoral tunnel 58 without a substantial amount of stress when the knee is placed in flexion between about 30 degrees and 110 degrees. It is understood that incisions must first be made in the soft tissue 55 surrounding the tibia 52 such that a tool may engage the tibia 52 and the femur 54 to form the tibial tunnel 56 and the femoral tunnel 58. Any suitable tool may produce the respective tunnels 56, 58 such as a pneumatic or electric drill or reamer. It is also understood that the femoral tunnel 58 is a blind tunnel. A blind tunnel is a tunnel which includes an entrance but no discernable exit, rather a blind tunnel terminates below the surface of the femur 54.

The size of the tibial tunnel 56 and the femoral tunnel 58 depends upon the size of the soft tissue replacement (described further herein) to be implanted into the patient. The larger the replacement needed, the larger the diameter of the tibial tunnel 56 and the femoral tunnel 58. The tibial tunnel 56 and femoral tunnel 58 may be of any required diameter, but are generally between about 5 and 18 millimeters. It would be understood, however, that if a larger diameter replacement is necessary, then larger diameter tunnels 56, 58 may be produced in the tibia 52 and femur 54 to receive the implant. Additionally, smaller tunnels 56, 58 may be used if only a smaller implant is necessary. In addition, the largest area of the insertion rod 26 will have a diameter substantially equal to the diameter of the tibial tunnel 56 and femoral tunnel 58. For example, if the insertion rod 26 was produced so that the guide portion 36, in particular the shoulder 41, form the largest diameter of the insertion rod 26, then the outside diameter of the guide portion 36 would be substantially equal to diameter of the tibial tunnel 56 and the femoral tunnel 58. Also, the body portion 28 may have a lesser diameter, or a taper towards the shoulder 41, to ease insertion and removal of the insertion rod 26. This ensures that the insertion rod 26, and particularly the slot 42, are substantially centered in the femoral tunnel 58 for the remaining procedure.

Figure 4:
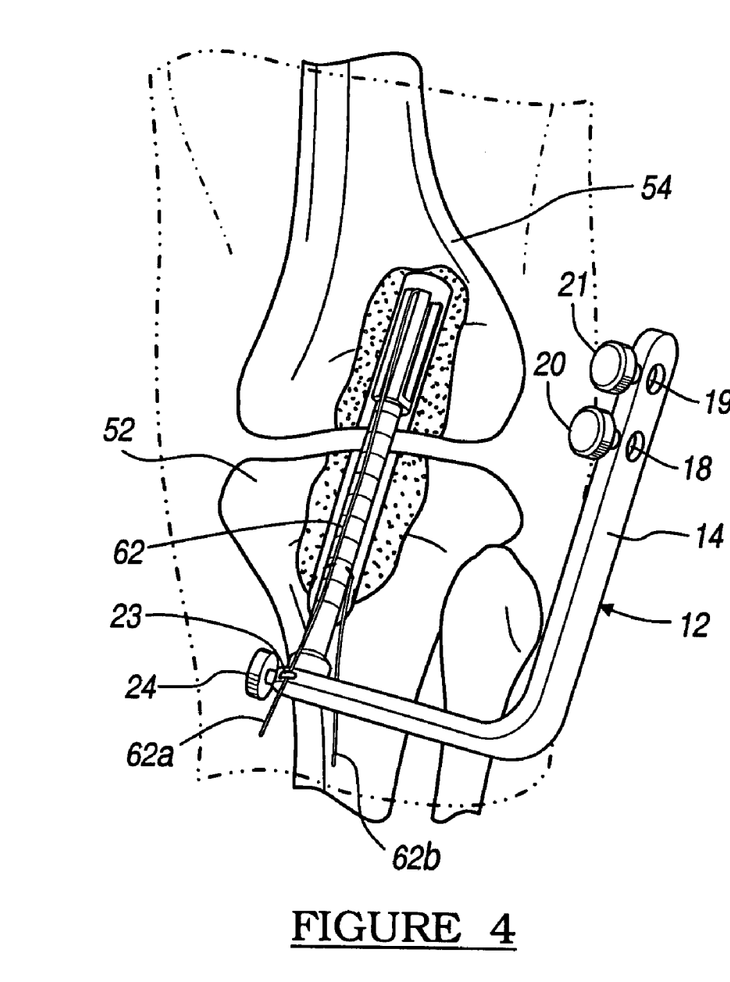
FIG. 4 is a perspective view of the insertion rod and U-Guide inserted into the tibia and femur tunnels with the flexible strand in place.

A flexible strand 62, having a trailing end 62*a* and a leading end 62*b*, is placed or pre-loaded into the flexible strand groove 44 and then the insertion rod 26 is inserted through the tibial tunnel 56 and into the femoral tunnel 58, as best shown in FIG. 4 (see also FIGS. 1 and 2). The flexible strand 62 may be any generally known strand suitable to the purpose such as a mono- or poly-filament suture, a flexible wire, or cord made of any suitable material. The flexible strand groove 44 allows the flexible strand 62 to be inserted through the tunnels 56, 58 without engaging the walls of the tunnels 56, 58. Generally the depth of the flexible strand groove 44 is at least equal to the diameter of the flexible strand 62. The flexible strand 62 is placed so that it reaches substantially to the end of the femoral tunnel 58 and the slot 42 creates an opening through the center of the femoral tunnel 58 through which an instrument may pass, while not interrupting the flexible strand 62 which has been inserted into the femoral tunnel 58 by the insertion rod 26. The flexible strand 62 is caught in the flexible strand notch 23. The flexible strand 62 is held in position during the insertion of the insertion rod 26 into the tunnels 56, 58 and during the remaining surgical procedure by the flexible strand notch 23. Any suitable means may be used to hold the flexible strand 62 in place relative to the L-Guide member 12 of the apparatus 10. The flexible strand notch 23, which holds the flexible strand 62 with friction, is merely exemplary of one appropriate means to hold the flexible strand 62 in place.

Figure 5:
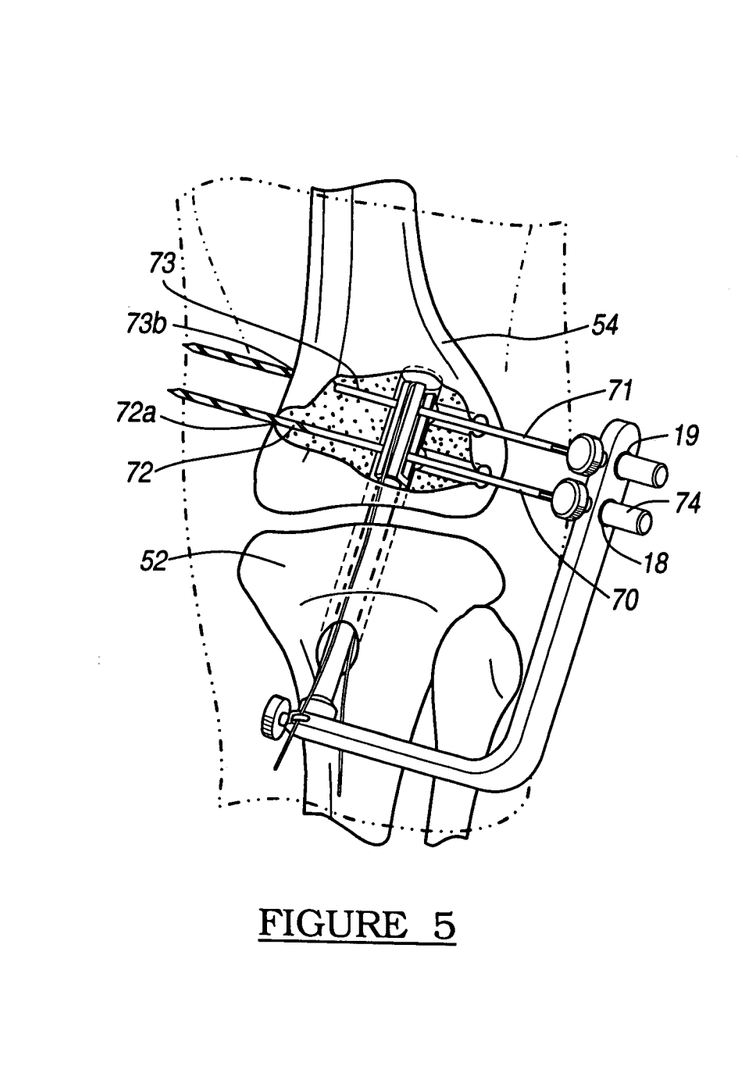
FIG. 5 is a view of the U-Guide and insertion rod in place with a pair of K-Wire Drill Points forming a transverse tunnel.

Referring generally to FIG. 5, once the insertion rod 26 has been inserted into the femoral tunnel 58, so that the flexible strand 62 is positioned properly, a device, such as a first drill bit or point 70 is used to produce a transverse tunnel 72 in the femur 54. The transverse tunnel 72 is formed transversely to the femoral tunnel 58 by using the first guide section 18. The second guide 19 is used to form a second transverse tunnel 73 using a second drill bit or point 71. The transverse tunnel 72 will include an insertion point 72*a* and an exit point 72*b*. It will be understood that an incision must first be made in the soft tissue 55 surrounding the femur 54, so that the drill bit or points 70 and 71 may engage the femur 54 to form the transverse tunnel 72. The drill points 70 and 71 may be powered by any appropriate device known in the art such as an electric or pneumatic drill. Furthermore, additional guide units or bullets 74, such as the U-Guide bullet produced by Arthotek, Inc. of Warsaw, Ind., may be used to ensure the proper orientation and depth of the drill points 70 and 71. The guide bullet 74 is inserted into the guide sections 18 and 19 and held in place with the set screws 20 and 21 to ensure the drill points 70 and 71 are properly aligned with the slot 42 when producing the transverse tunnels 72.

The transverse tunnels 72 and 73 are produced through the entire width of the femur 54 so that the drill points 70 and 71 exits the femur 54 producing the exit points 72*b* and 73*b*. This allows the drill points 70 and 71 to be removed through the exit points 72*b* and 73 at the appropriate time. While the apparatus 10 is still in place, a cannulated reamer (not shown) enlarges a portion of the transverse tunnel 72. The reamed tunnel 75 receives the pin 84 (described herein). The reamed tunnel 75 does not extend the length of the transverse tunnel 72. The second drill point 71 forms a removable suture bearing surface 76, while the first drill point 70 has a soft tissue bearing surface 77.

Figure 6:
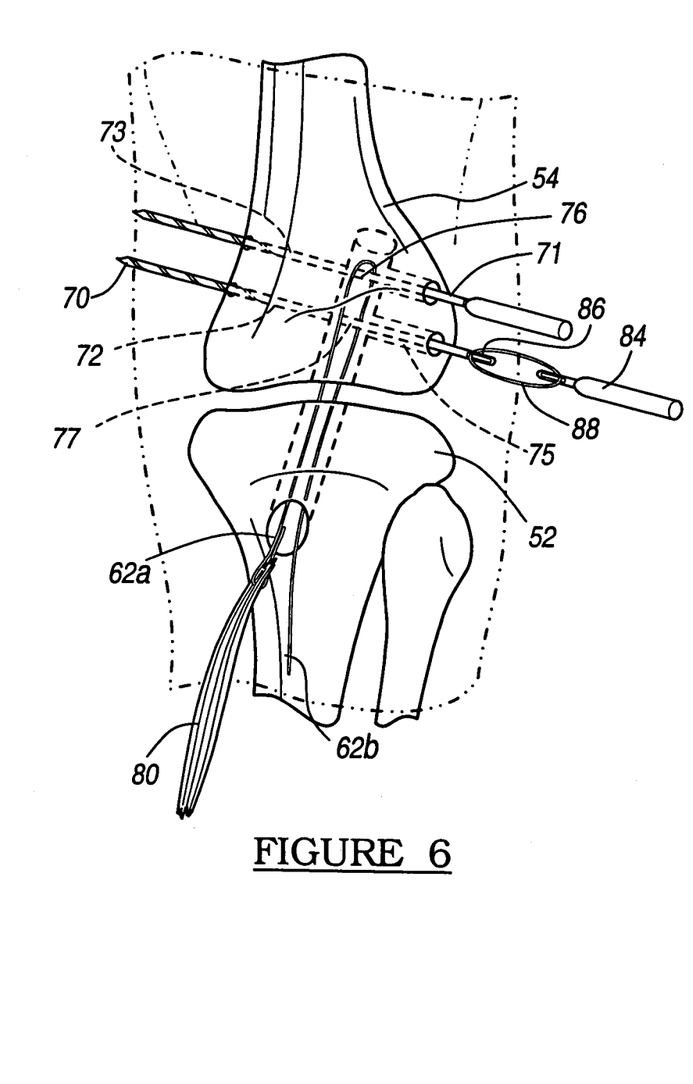
FIG. 6 is perspective view of the first and second K-Wire Drill Points with the flexible strand affixed to a soft tissue replacement and draped over the second K-Wire Drill Point.

After the reamed tunnel 75 is produced, the apparatus 10, is removed as particularly shown in FIG. 6. Once the apparatus 10 has been removed, the drill point 70 remains in the transverse tunnel 72. A soft tissue replacement 80 is affixed to the trailing end 62*a* of the flexible strand 62. The soft tissue replacement may be any suitable replacement such as a hamstring portion, an allograft tissue replacement, a xenograft tissue replacement, or an artificial soft tissue replacement which may be produced from materials such as polymers or metal.

Figure 7:
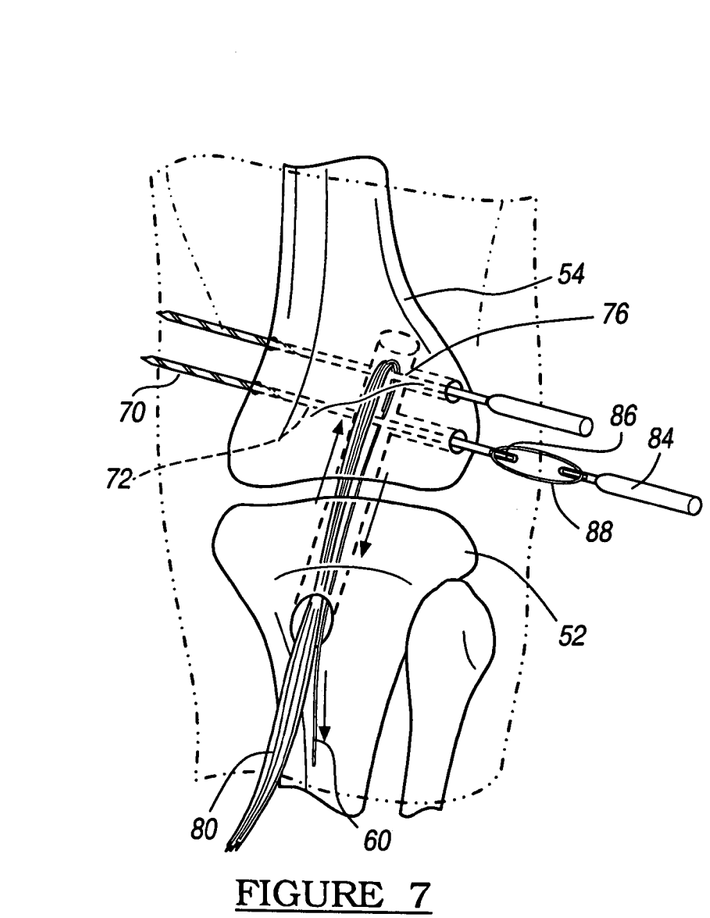
FIG. 7 depicts the second K-Wire Drill Point removed with the soft tissue replacement draped over the first K-Wire Drill Point.
Figure 8:
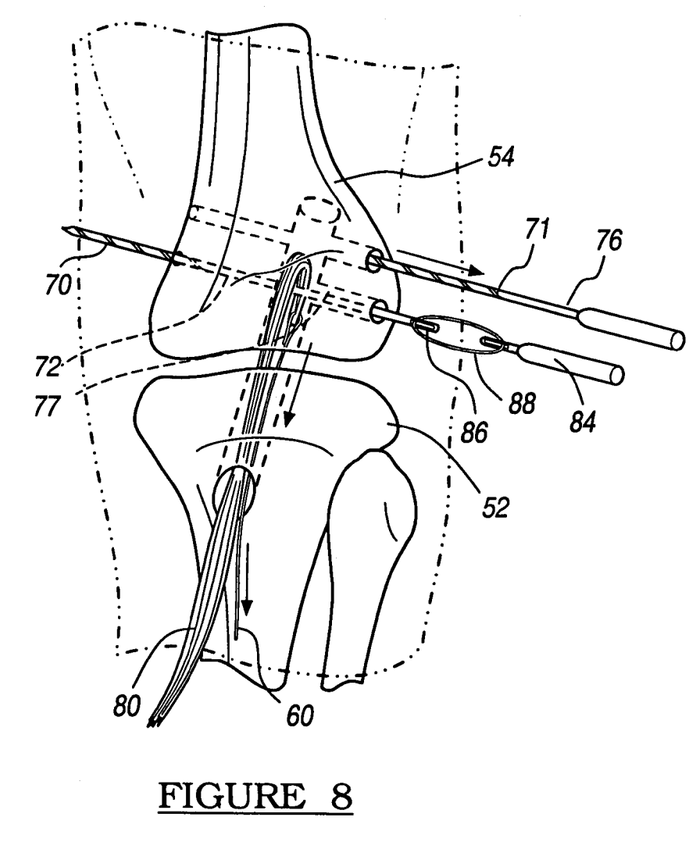
FIG. 8 is a perspective view of the soft tissue replacement pulled over the K-Wire and out through the tibial tunnel.
Figure 9:
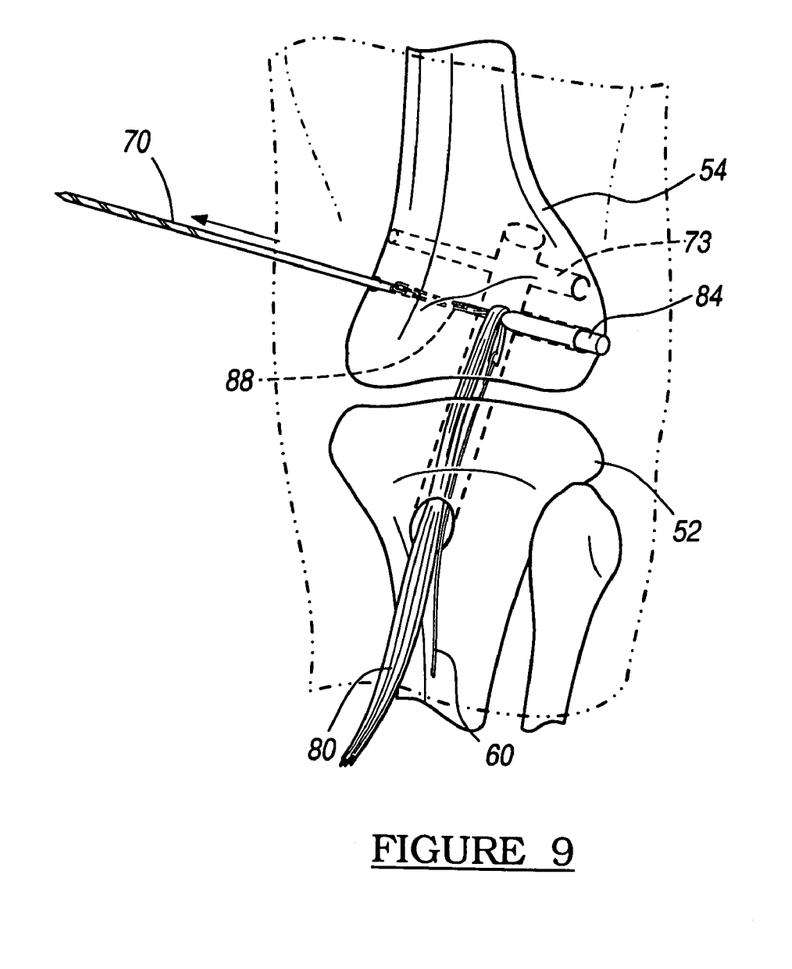
FIG. 9 is a perspective view of the soft tissue replacement in place and the ACL Cross Pin set in place in the transverse tunnel in the femur.

As shown in FIG. 7, after the soft tissue replacement 80 has been affixed to the trailing end 62*a*, the leading end 62*b* of the flexible strand 62 is pulled over the suture bearing surface 76 drawing the soft tissue replacement 80 first through the tibial tunnel 56 and then through the femoral tunnel 58 adjacent to and preferably over the first drill point 70 and up to the second drill point 71. At this point, the second drill point and suture bearing surface 76 is removed and the flexible strand and soft tissue is pulled to pull the soft tissue over the first drill point 70 and associated soft tissue bearing surface 77, back down the femoral tunnel 58, and out through the tibial tunnel 56. This produces a loop of the soft tissue replacement 80 over the soft tissue bearing surface 77 of the first drill point 70 inside of the femoral tunnel 58. After being looped over the first drill point 70, the two free ends 80*a* and 80*b* of the soft tissue replacement 80 extend from the tibial tunnel 56 adjacent to the tibia 52.

After the soft tissue replacement 80 has been looped over the first drill point 70, an ACL cross pin or pin 84 is pulled into place in the reamed tunnel 75. The drill point 70 generally includes an eyelet 86 which will allow the attachment of the pin 84 to the drill point 70. Generally, the pin 84 is attached to the eyelet 86 through a second flexible strand 88 or other appropriate means. After the pin 84 is attached to the eyelet 86, the drill point 70 is pulled through the transverse tunnel 72, through the loop of the soft tissue replacement 80 and out the exit point 72*b*. This pulls the pin 84 into position and fixes it within the transverse tunnel 72, as particularly shown in FIG. 9. Once the pin 84 has been fixed in place in the transverse tunnel 72, the attached flexible strand 88 may be cut or otherwise disengaged from between the eyelet 86 and the pin 84. The drill point 70 is then freely removed from the transverse tunnel 72. This leaves the pin 84 lodged into the transverse tunnel 72 which may be locked in place with either portions of the pin 84 or through any other appropriate locking means. Although any appropriate means may be used to hold pin 84 in the reamed tunnel 75, the pin 84 may include a square end to hold pin 84 in place. The pin 84 may also be threaded such as the device described in U.S. Pat. No. 5,674,224 entitled "Bone Mulch Screw Assembly For Industrial Fixation of Soft Tissue Soft tissue replacements And Method For Using Same" to Stephen M. Howell et al. incorporated herein by reference.

Figure 11:
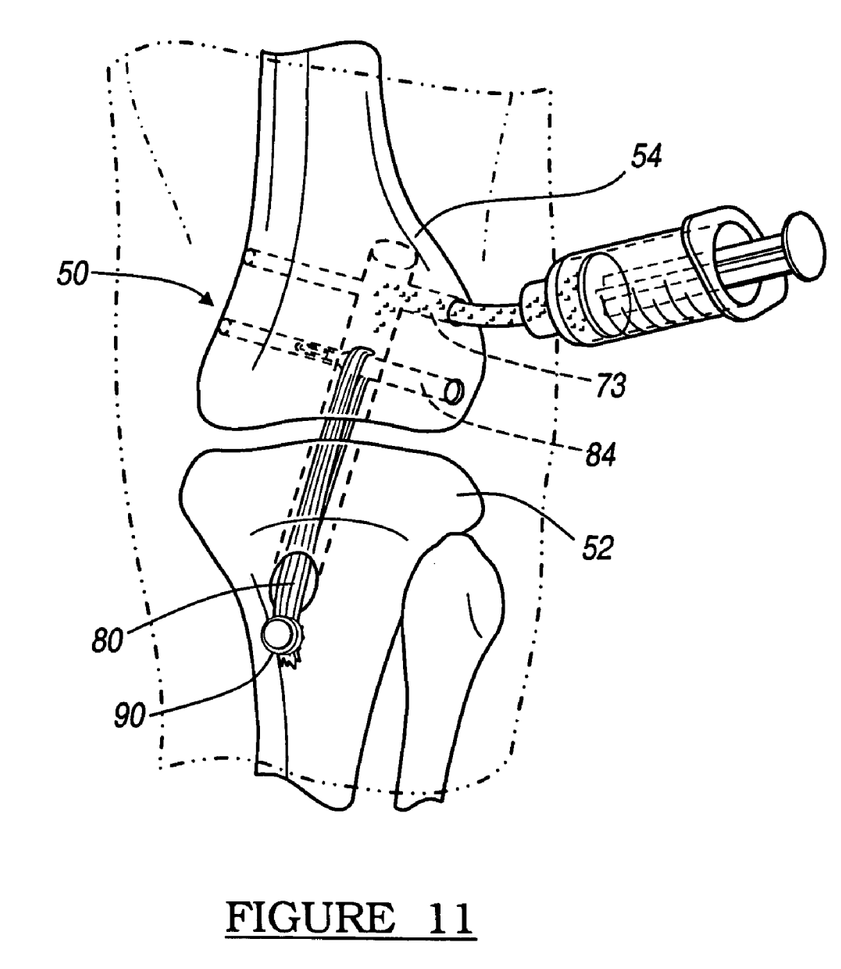
FIG. 11 depicts the injections of into a transverse tunnel.

As shown in FIG. 11, the second transverse tunnel 73 forms an aperture which can be used to inject biologic materials such as platelets, bone chips, or allograph materials into the tunnel 56. Additionally, the second transverse passage 73 can be used to inject bone cement into the femoral tunnel 58 and about pin 84.

Figure 10:
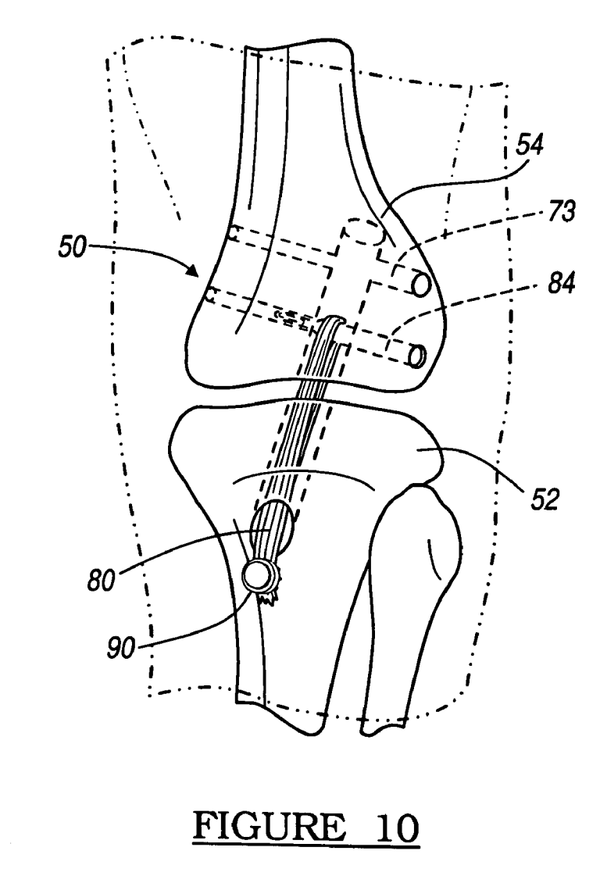
FIG. 10 is a deep view of the knee with an ACL replacement having its free ends affixed to the tibia and the femoral end affixed over the ACL Cross Pin.

Because the pin 84 has been lodged in the transverse tunnel 72, and the soft tissue replacement 80 is looped over the pin 84, only the free ends 80a and 80b need to be secured to the tibia 52 to complete the implantation. A staple 90 is used to affix the free ends 80a and 80b of the soft tissue replacement 80 to the tibia 52, as best shown in FIG. 10. It will be understood, however, that any appropriate means may be used to affix the free ends 80a, 80b to the tibia 52 such as U.S. Pat. No. 5,674,224 entitled "Bone Mulch Screw Assembly For Industrial Fixation of Soft Tissue Soft tissue replacements And Method For Using Same" to Stephen M. Howell et al.; U.S. Pat. No. 6,280,472 B1 entitled "Apparatus And Method For Tibial Fixation Of Soft Tissue" to James A. Boucher et al.; and U.S. Pat. No. 5,931,869 entitled "Apparatus And Method For Tibial Fixation Of Soft Tissue" to James A. Boucher et al. each incorporated herein by reference. Once the free ends 80a and 80b of the soft tissue replacement 80 are affixed to the tibia 52, the soft tissue replacement 80 securely attaches the tibia 52 and the femur 54 substantially as a natural ACL would.

It will be understood that any appropriate means may be used to affix the soft tissue replacement 80 in the femoral tunnel 58. The pin 84 is merely exemplary of any appropriate device to affix the soft tissue replacement 80 in the femoral tunnel 58. Any commonly known screw or other fixation device may be used to fix the soft tissue replacement 80 in the femoral tunnel 58. It will also be understood that the soft tissue replacement 80 may be pulled over the pin 84 after the pin 84 has been lodged in the transverse tunnel 72. In particular, if the pin 84 is smooth, the soft tissue replacement 80 may be pulled over the pin 84 without damaging the soft tissue replacement 80 itself. The drill point 70 is simply removed from the transverse tunnel 72 before the soft tissue replacement 80 is pulled into the femoral tunnel 58.

It will also be understood that the method for performing the described procedure may be altered but remain within the scope of the presently claimed invention. For example the flexible strand 62 may looped over the insertion rod 26 such that the two free ends 62a and 62b are on one side and a loop of the flexible strand is formed on the other side of the insertion rod 26. Thus the soft tissue replacement 80 may be affixed to both free ends 62a and 62b or placed through the loop and then pulled over the insertion rod 26.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method of surgically coupling a soft tissue replacement into a first tunnel defined within a bone comprising:
   inserting an insertion rod comprising a guide member into the first tunnel, wherein a flexible strand is pre-loaded in the form of a loop onto said guide member;
   forming a second tunnel transverse and through said first tunnel and said loop;
   forming a third tunnel transverse and through said first tunnel and said loop;
   placing a soft tissue bearing member within said second tunnel so as to traverse said first tunnel; and
   placing a removable flexible strand bearing element within said third tunnel so as to traverse said first tunnel.

2. The method of claim 1, further comprising affixing said insertion rod to an external fixture such that said insertion rod is aligned with said external fixture.

3. The method of claim 2, wherein the step of forming said second tunnel includes aligning a drill bit using said external fixture.

4. The method of claim 3, further comprising the step of forming said first tunnel in a first bone member.

5. The method of claim 1, further comprising the steps of:
   affixing a soft tissue to the soft tissue bearing member in said first tunnel;
   removing the flexible strand bearing element from the third tunnel;
   pulling said soft tissue over said soft tissue bearing member in said first tunnel and back out said first tunnel; and
   affixing the soft tissue to a bone.

6. The method according to claim 5 further including pulling said soft tissue from said soft tissue bearing member to said flexible strand bearing element.

7. The method of claim 5 further including injecting biological materials into the first tunnel.

8. The method according to claim 5 further including injecting biological materials through the third tunnel into the first tunnel.

9. The method according to claim 8 further including coupling a syringe to the third tunnel.

10. The method of claim 1, wherein said step of forming said second tunnel comprises aligning a first tunnel forming device to form said second tunnel using said insertion rod.

11. A method of surgically coupling a soft tissue replacement into a first tunnel defined within a bone comprising:
    inserting a first portion of an insertion mechanism into the first tunnel, wherein a flexible strand is pre-loaded in the form of a loop onto said insertion mechanism;
    forming a second tunnel generally perpendicular to and coupled to said first tunnel;
    forming a third tunnel generally perpendicular to and coupled to said first tunnel;
    placing a soft tissue bearing member within said second tunnel after inserting the first portion of the insertion mechanism so as to at least partially traverse said first tunnel; and
    placing a flexible strand bearing element within said third tunnel so as to at least partially traverse said first tunnel, wherein said flexible strand at least partially surrounds the flexible strand bearing element and the soft tissue bearing member.

12. The method of claim 11, further comprising affixing said insertion mechanism to an external fixture such that said insertion mechanism is aligned with said external fixture.

13. The method of claim 12, wherein forming said second tunnel includes aligning a drill bit using said external fixture.

14. The method of claim 11, further comprising forming said first tunnel in a first bone member.

15. The method of claim 11, further comprising the steps of:
- affixing a soft tissue replacement to a first end of said flexible strand; and
- pulling said soft tissue to the soft tissue bearing member into said first tunnel;
- removing said flexible strand bearing element from the third tunnel;
- pulling a portion of said soft tissue over said soft tissue bearing member in said first tunnel and back out said first tunnel; and
- affixing the soft tissue to a bone.

16. The method according to claim 15 further including pulling said soft tissue from said soft tissue bearing member to said flexible strand bearing element.

17. The method of claim 15 further including injecting biological compatible materials into the first tunnel.

18. The method according to claim 15 further including injecting biological materials through the third tunnel into the first tunnel.

19. The method according to claim 18 wherein forming the second tunnel is forming a tunnel having a first diameter, and forming a third tunnel is forming a tunnel having a second diameter, wherein the second diameter is smaller than the first diameter.

20. The method of claim 11, wherein said step of forming said second tunnel comprises aligning a second tunnel forming device with said insertion mechanism.

* * * * *